US 6,605,808 B2

(12) United States Patent
Mickan et al.

(10) Patent No.: US 6,605,808 B2
(45) Date of Patent: Aug. 12, 2003

(54) DIAGNOSTIC APPARATUS USING TERAHERTZ RADIATION

(75) Inventors: Samuel Mickan, Adelaide (AU); Derek Abbott, Adelaide (AU)

(73) Assignee: Luminis PTY LTD, Adelaide (AU)

( * ) Notice: Subject to any disclaimer, the term of this patent is extended or adjusted under 35 U.S.C. 154(b) by 20 days.

(21) Appl. No.: 10/016,489

(22) Filed: Dec. 10, 2001

(65) Prior Publication Data

US 2002/0074500 A1 Jun. 20, 2002

(30) Foreign Application Priority Data

Dec. 15, 2000 (AU) .............................................. PR2139

(51) Int. Cl.[7] .............................................. G01B 11/00
(52) U.S. Cl. .................................................... 250/341.8
(58) Field of Search ............................ 250/341.1, 341.8

(56) References Cited

U.S. PATENT DOCUMENTS

| 5,543,960 A | 8/1996 | Carrig et al. |
| 5,623,145 A | 4/1997 | Nuss |
| 5,710,430 A | 1/1998 | Nuss |
| 5,894,125 A | 4/1999 | Brener et al. |
| 5,939,721 A | 8/1999 | Jacobsen et al. |
| 5,982,493 A * | 11/1999 | Lehnen et al. ............... 356/613 |
| 6,519,076 B2 * | 2/2003 | Fisher et al. ................. 359/326 |
| 6,525,862 B2 * | 2/2003 | Fisher et al. ................. 359/278 |

* cited by examiner

*Primary Examiner*—G. Bradley Bennett
(74) *Attorney, Agent, or Firm*—R. Neil Sudol; Henry D. Coleman; William J. Sapone

(57) ABSTRACT

A diagnostic apparatus including a terahertz generator taking the form of a femtosecond laser exciting either an optoelectric crystal of a photoconductive dipole antenna the terahertz radiation is directed onto a target preferably held close by or abutting an enclosure including a reflection receiving window and housing terahertz detector for detecting terahertz radiation. Preferably the terahertz radiation generator forms part of the receiving window. The enclosure has a modified atmosphere to permit ready transmission of terahertz radiation. A beam splitter is positioned between the laser and the terahertz generator to split off a probe laser beam from the terahertz inducing laser radiation which is also directed to the detector means. The output from the detector being determined by the amplitude of that part of the reflected teraherz radiation wave coaligned with the probe laser at the detector. A delay is positioned in the probe laser path to altering the length of the probe laser path over terahertz subwavelength distances so that different parts of the terahertz wave form can be interrogated by the probe laser to thereby ascertain the shape and dimensions of the reflected terahertz radiation.

24 Claims, 3 Drawing Sheets

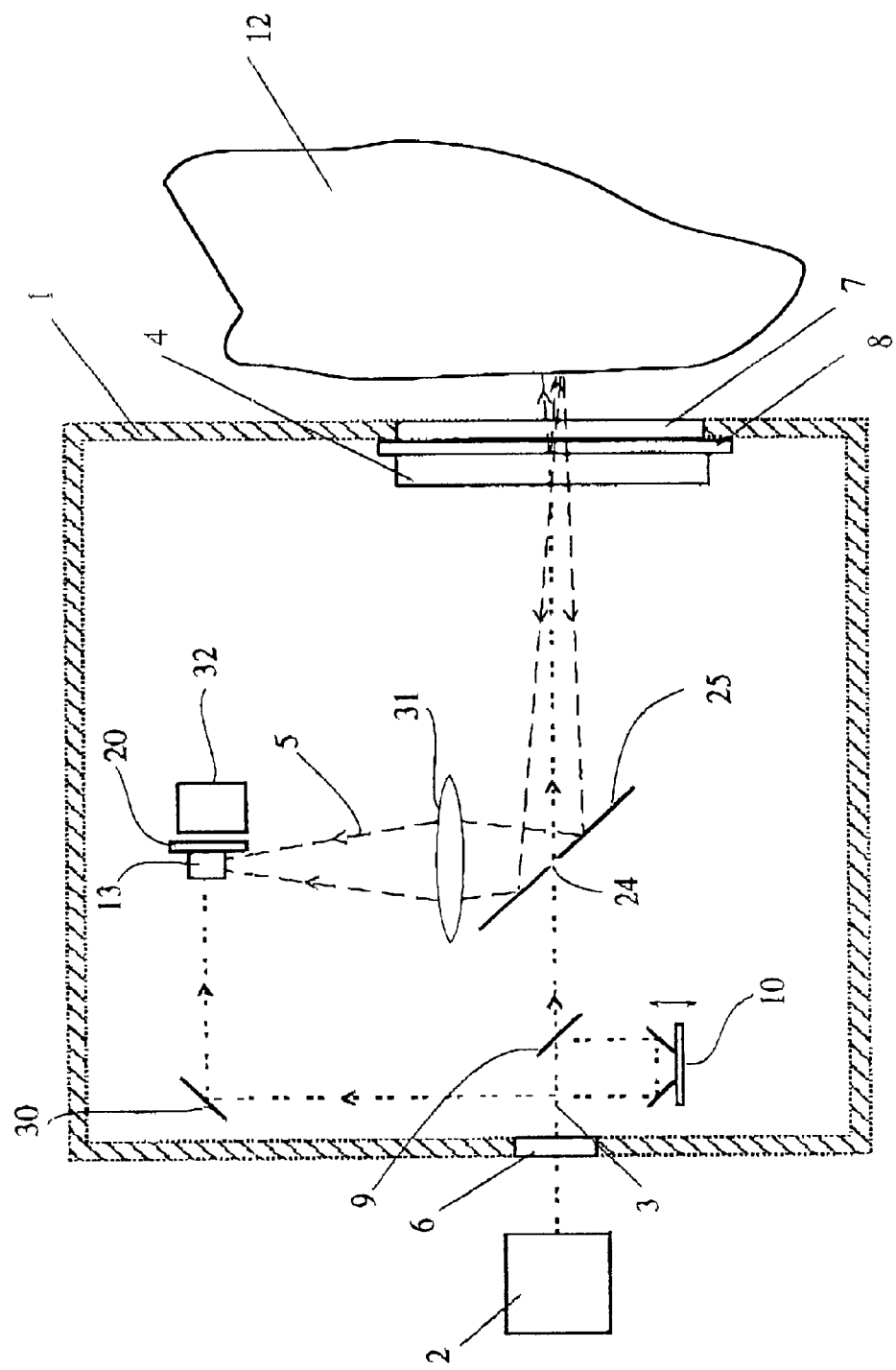

DIAGNOSTIC APPARATUS USING TERAHERTZ RADIATION

FIELD OF THE INVENTION

This invention relates to a diagnostic apparatus which utilises terahertz radiation. Embodiments of the invention may be useful for a range of diagnostic methods providing spectroscopic and tomographic information. The specific applications of the apparatus may be diverse and include, again not exhaustively, medical imaging, chemical analyses and non-destructive testing.

BACKGROUND

Terahertz (T-ray or THz) radiation lies on the boundary of electronics (millimeter waves) and photonics (infrared). The terahertz spectrum encompasses the wavelenths in the range of 3 mm to 15 $\mu$m although it will be appreciated that these limits are indicative rather than absolute.

Terahertz radiation exhibits a large range of modifications on passage through varying materials or on reflection from materials. Such changes include attenuation or partial attenuation of different frequencies of the waveform and other alteration of the waveform depending upon the material through which the radiation or pulses pass. Terahertz radiation interacts strongly with polar molecules, a prime example being water. Water molecules absorb terahertz waves, on the one hand limiting penetration of the radiation in moist substances, and on the other hand making it readily detectable even in very low concentrations. It can be used for detecting low concentrations of polar gases. However, terahertz radiation will penetrate non-polar substances such as fats, cardboard, cloth and plastics with little attenuation. Materials including organic materials have varying transmission, reflection and absorption characteristics to terahertz radiation.

Accordingly, use of terahertz radiation can indicate the presence of different materials. Terahertz radiation has been used for an increasing range of chemical sensing applications, including biomedical diagnostics (Han et al. (2000), Optics letters 25(4) 242–244) semiconductor device diagnostics (Walecki et a., (1993) Applied Physics letters 63(13) 1809–1811), trace gas analysis (Jacobsen Optics letters 21(24) 2011–2013) moisture analysis for agriculture (Hadjiloucas et al., (1999) IEEE Transactions on Microwave Theory and Techniques 47(2) 142–149) quality control of packed goods (May (1997) New Scientist 154 (2083) 22) inspection of artwork and inspection of internal structure of smart cards (Nuss (1996) IEEE Circuits and Devices 12(2) 25–30). Having low average power, T rays are particularly attractive for medical applications, where it is important to avoid damaging the sample.

Terhertz chemical sensing has in recent years been applied to a number of biological problems. As indicated above T rays are strongly attenuated by moist tissue because of water absorption. This has limited medical applications to dry or thin samples. Toshiba, for example, have explored T-ray images of human teeth (Arnone et al (1999) "Applications of terahertz (THz) technology to medical imaging," in Proceedings of SPIE—Conference on Terahertz Spectroscopy and Applications vol 3828 209–219 SPIE (Munich Germany)). The T-ray data revealed differences between the enamel, the enamel and dentine and a cavity. T-ray images of living plant leaves and thin samples of wood have been studied to show wear and density profiles (Koch "THz imaging: Fundamentals and biological applications" in Proceedings of SPIE—Conference on Terahertz Spectroscopy and Applications vol 3828 202–208 SPIE (Munich Germany). Rice University has shown terahertz profiles of burnt chicken tissue (Mittleman et al (1999) Applied Physics B Lasers ad Optics 68(6) 1085–1094) and thin slices of Spanish ham have also been studied (Ferguson & Abbott (2000) "Signal processing for t-ray bio-sensor systems" in Proceedings of SPIE's 2000 Symposium on Smart materials and MEMS, SPIE (Melbourne, Australia)). The problems with biological imaging are resolution, penetration and speed. The resolution is limited by wavelength in the far field, giving about 0.3 mm resolution at 1 terahertz, which will be sufficient for many biological applications. Depth penetration is a greater problem, even for reflective spectroscopy. Depth penetration can be improved by increasing the terahertz power and reducing the path length. Lastly, the imaging speed is important for living samples that tend to move. A CCD two dimensional imaging technique has been used to minimise motion between the imager and the sample.

Both transmissive and reflective geometries have been used or at least proposed in terahertz devices. Transmission geometries include placing a sample between the transmitter and the detector of the terahertz radiation. This often requires that the terahertz radiation follows a long path length. Where the path is through an atmosphere containing water vapour there is poor terahertz radiation transmission and so detection is made more difficult if at all possible. Similarly reflective geometries have suffered from the utilisation of long path lengths. To alleviate this problem it has been proposed in transmission geometries to place the transmitter, sample and detector within a container in which the atmosphere permits ready transmission of terahertz radiation. This restricts the application of terahertz to samples that can be fitted within the container and are not adversely affected by the atmosphere within the container, and which therefore generally excludes medical application.

A further problem is that terahertz radiation is typically low powered and even a few millimeters of moist dermal tissue can effectively block transmission.

It is a proposed object of this invention to provide a diagnostic apparatus to obviate or minimise at least one of the aforementioned problems, or at least provide the public with a useful choice.

SUMMARY OF INVENTION

The invention may be said to reside, not necessarily in the broadest or only form, in a diagnostic apparatus including a terahertz generator for generating terahertz radiation, and an enclosure including a reflection receiving window and a terahertz detector for detecting terahertz radiation, the terahertz generator directing terahertz radiation onto a target, reflected terahertz radiation being reflected through the reflection receiving window into the enclosure and to the detector, a modified atmosphere being provided within the enclosure to permit ready transmission of terahertz radiation. The terahertz radiation may be generated inside or on a surface of the enclosure, and is directed out from the reflection receiving window. Preferably the terahertz generator is radiated by terahertz inducing laser radiation directed thereonto by a laser, the terahertz generator being either a terahertz generating electro-optic crystal or a terahertz generating photoconductive dipole antennna. The terahertz generator may be a terahertz generating electro-optic crystal, and preferably the terahertz generating crystal forms at least part of the reflection receiving window. A beam splitter may be positioned between the laser and the terahertz generator to split off a probe laser beam from the terahertz inducing laser radiation, said probe laser beam travels through a probe laser path to the detector means, the detector providing a quantitative output, the output being determined by the amplitude of that part of the reflected teraherz radiation wave coaligned with the probe laser at the detector. Preferably a delay positioned in the probe laser path said delay altering a length of the probe laser path over terahertz subwavelength distances to thereby vary the co-alignment of the probe beam and the reflected terahertz radiation wave.

BRIEF DESCRIPTION OF THE DRAWINGS

To assist in the understanding of the invention a preferred embodiment will now be described with reference to the accompanying drawing:

FIG. 3 is a schematically sketched cross sectional view of a third embodiment of diagnostic apparatus according to this invention.

DETAILED DESCRIPTION OF THE ILLUSTRATED EMBODIMENT

Figure 1:
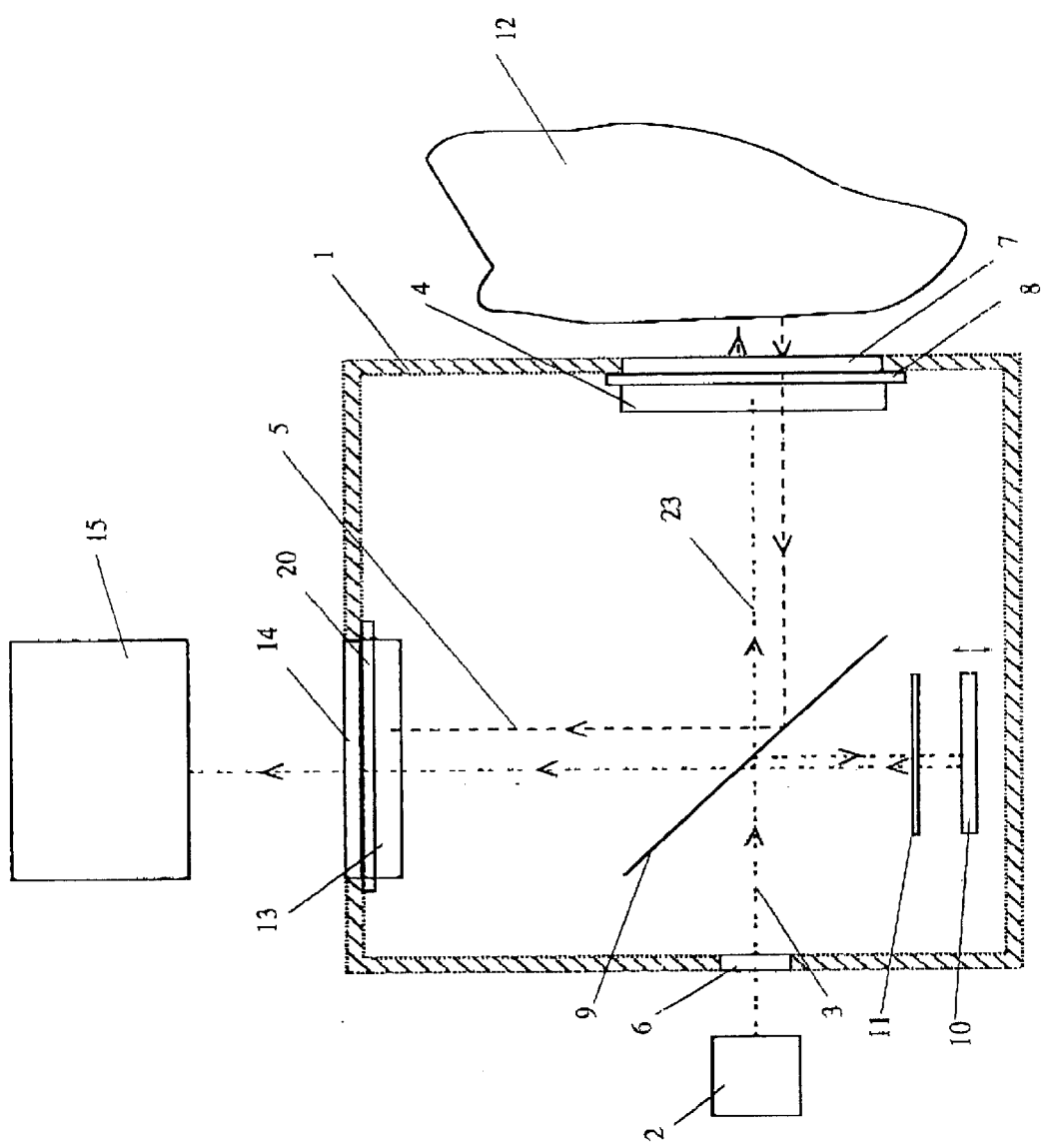
FIG. 1 is a schematically sketched cross sectional view of a first embodiment of a diagnostic apparatus according to this invention.

Similar reference characters indicate corresponding parts throughout the several views of the drawings.

Dimensions of certain of the parts shown in the drawings may have been modified and/or exaggerated for the purposes of clarity or illustration.

It will be appreciated that the diagnostic apparatus operates upon reflected terahertz radiation rather than in a transmission mode. By placing the sample close to or abutting the reflection receiving window the path length travelled by the terahertz radiation outside of the enclosure need not be long. Accordingly, the diagnostic apparatus may be used with samples that would be otherwise too big or adversely effected by an atmosphere that allows ready transmission of terahertz radiation. One such example is the application of terahertz radiation to testing living human beings including imaging internal structures for diagnostic purposes or for highlighting different cells within a body.

The present invention addresses the losses and distortions caused by terahertz radiation travelling through air by minimising the path length. Water in the atmosphere slightly reduces the amplitude of the terahertz radiation and imparts a ringing to the waveform. The effects of water vapour can be removed by drying or evacuating the radiation path. Using reflection geometry, the path length can be minimised and a substantial portion of the terahertz path can traverse the sealed enclosure which is conducive to terahertz radiation transmission.

Terahertz radiation may be produced by two approaches. In a first approach a femtosecond laser is directed into an electro-optic crystal, typical examples of these include zinc blend crystal such as zinc telluride or gallium arsenide crystals. A second approach is to utilise a photoconductive dipole antenna. Either of these two approaches may be applicable to the present invention, although it is preferred to use an electro-optic crystal as a means of generating terahertz radiation. Terahertz generation systems are described in Bass et al., (1962) Physical Review Letters 9(11):446–448, Xu et al., (1992) Applied Physic letters 61(15) 1784–1786, and U.S. Pat. No. 5,952,818 to Zhang et al., all of which are incorporated herein by reference.

The terahertz generator may include a femtosecond laser directing laser radiation onto a terahertz generating crystal which under the influence of the laser radiation emits terahertz radiation. The terahertz generating crystal is preferably at least part of the reflection receiving window, or adjacent the reflection receiving window. In the alternative the terahertz generator includes a femtosecond laser directing laser radiation onto a photoconductive dipole antenna (PDA), which photoconductive dipole antennae is adjacent or formed into the reflection receiving window. The close proximity of the source of terahertz to the reflection receiving window minimises attenuation that might occur within the enclosure.

Preferably the sample target of the terahertz irradiation is held close to or abutting the reflection receiving window. It might be desired to have the target positioned at a short distance away from the source of the terahertz irradiation so that an appreciable area of the target is irradiated, such that reflection from the appreciable area can be detected, however at diminished intensity when compared to a smaller area. In the alternative the target might be held closer so that only a smaller area is irradiated at higher intensity and thus generally better resolution, the target may be moved relative to the reflection receiving window over time and an extended image might be built up as a result of measurement of reflection from a number of 'points'.

Where the source of the terahertz is part of the wall and the sample can be held at a position spaced from the terahertz source by a distance less than the wavelength of the terahertz, a higher resolution can be achieved using near field imaging. A method of employing near field imaging is described in U.S. Pat. No. 5,894,125 to Benner and Nuss, which is incorporated herein by reference.

Where the terahertz source is from an electro-optic crystal the terahertz radiation can readily be reflected back through the crystal without appreciable attenuation and thus the terahertz generating crystal can also be at least part of the reflection receiving window.

It is preferred to use terahertz radiation having relatively high frequency radiation. This is desirable because the higher frequency provides for a higher resolution than lower frequency radiation. The terahertz radiation may have a bandwidth spanning the range of 0.1 to 10 THz, which corresponds to about 3 to 0.1 millimeters in wavelength. The pulse of the terahertz radiation is also preferably short, and thus preferably in the order of $10^{-12}$ seconds, which therefore has a high peak power, and short time resolution.

There are practical difficulties in direct detection of terahertz pulses, and therefore indirect methods are most suitably employed. The detection of reflected terahertz radiation is typically achieved using a detector electro-optic crystal or by using a detector PDA.

In one form the detector means thus includes a second electro-optic crystal which in response to terahertz radiation alters its optical characteristics such that laser radiation directed upon the detector crystal reveals the terahertz radiation. The optical characteristic may include the polarisation experienced by laser radiation passing through the crystal.

It is preferred that the laser radiation is split into an actuation laser beam and a probe laser beam. Thus for example an electro-optic crystal is used, the actuation laser beam is directed to the terahertz generating electro-optic crystal, to forms terahertz radiation which is directed to the target and reflected radiation is then directed to the detector electro-optic crystal. The probe laser radiation is diverted through a delay means such as a delay stage and then to the detector electro-optic crystal, the incidence of the probe laser beam is coaligned with the reflected radiation beam, so as to meet within the detector electro-optic crystal. A polarity filter is positioned between the detector electro-optic crystal and a photodetector such that the probe laser beam does not pass through the polarity filter unless the detector electro-optic crystal causes the probe laser beam to rotate.

The terahertz radiation causes polarisation of the probe laser beam to rotate and the degree of rotation is proportion to the amplitude of the reflected terahertz radiation. The extent to which the probe laser beam is transmitted through the polarity filter is a measure of the amplitude of the portion of the terahertz wave that was aligned with the probe laser beam.

The delay means is preferably adjustable so that the path length of the probe laser beam can be varied relative to the path length of the actuation laser beam, and the reflected terahertz radiation. The accuracy of adjustment of the delay stage is preferably such that the stage can be adjusted to subwavelength increments whereby alignment of the probe laser waveform can be made with various parts of the reflected terahertz waveform so that the dimensions and preferably shape of the wave can be ascertained.

Some detailed aspects of the constructions beam splitting and detector might be as described in U.S. Pat. No. 5,952,818 to Zhang et al. which is incorporated herein by reference.

Alternatively a detector PDA may be used whereby reflected terahertz radiation together with the probe laser when co-aligned can provide for an electric pulse, and whereby variation in the pathlength of the probe laser can be used to ascertain characteristics of the reflected terahertz radiation. Significantly the detector in this form may be provided as an array of PDAs especially where the target is spaced from the terahertz source so that an appreciable area of the target reflects terahertz radiation so that a two dimensional image can be built up without requiring scanning of the target.

In another form, the apparatus includes a transmission means for laser radiation created outside the enclosure to transmit laser radiation into the enclosure and into the terahertz generating electro-optic crystal or alternatively a terahertz generating PDA. Accordingly, the femtosecond laser may be positioned outside the enclosure and the laser radiation transmitted through a transmissive window into the enclosure. Alternatively, an optical fibre may be used to conduct the laser radiation to the terahertz generating electro-optic crystal or terahertz generating PDA without necessarily being transmitted through the enclosure, but terahertz beam travel only a minimal distance before entering the enclosure.

The co-alignment of the reflected terahertz beam and the probe laser beam may be such that the probe beam and the reflected terahertz radiation are co-incident, alternatively however the probe beam may be incident somewhat transverse of the incidence of the reflected terahertz radiation. The delay stage may be adjusted so as to co-align the probe beam and the reflected terahertz radiation such that the terahertz radiation influences the polarity of the probe pulse.

The delay stage is variable such that the path lengths of the probe beam and the sum of the actuation beam and terahertz radiation can be aligned, or varied temporally so that different parts of the terahertz radiation wave can be measured to provide an output that reflects the wave shape of the reflected terahertz radiation.

The detector means may include a beam splitter means between the laser and the teraherz generator directing a portion of the laser radiation onto a beam directing means which directs the laser radiation upon the terahertz detector. In one form the beam directing means is a mirror which reflects the laser radiation through the beam splitter means onto the terahertz generator, and the reflected terahertz radiation is directed by the beam splitter means to the detector and thereby is co-aligned with the laser radiation.

The beam directing means includes a delay means to alter the optical path distance of the probe laser pulse before reaching the second crystal. Altering the optical path distance allows phase and magnitude data together with temporal data to be gained. The delay means may be a delay stage and may take a number of forms but preferably includes stage mounted mirrors that can be adjusted mechanically to vary the path length of the probe laser pulse.

The reflection receiving window may be formed at least in part by the terahertz generating crystal which then permits passage of reflected terahertz radiation as well as generating the transmitted terahertz radiation. Although one may wish to use a separate terahertz beam generating arrangement which is separate from the detection arrangement, but preferably optically connected so that laser radiation can be split into the actuation beam and a probe beam. Thus the actuation beam might be directed through an optically conducting fibre with a zinc telluride tip located relative to the target and reflection receiving window to direct a terahertz pulse to reflect off of the target through the reflection receiving window.

The electro-optic crystals used for the generation and detection of terahertz radiation might be of any suitable electro-optic material and those where the behaviour of the terahertz radiation and laser radiation are matched. Electro-optic materials known to be most suitable for this purpose include zinc telluride, or gallium arsenide. Other good electro-optic materials may also be used.

In one form the atmosphere within the enclosure is evacuated. Alternatively, the atmosphere within the enclosure may consist primarily of a non-polar gas which in an economic form might be nitrogen. Thus the enclosure might simply be flushed with nitrogen to substantially replace the air present.

As indicated above water has a significant influence on terahertz pulses, and whilst some moisture within the enclosure is workable it is preferred that the moisture is kept low and thus might have a level less than about 0.1% water.

In one form the laser produces laser radiation pulses of pulse width less than 100 fs. In another the laser produces laser radiation pulses of pulse width less than 20 fs. The smaller the pulse width allows the system to have a higher bandwidth. The wavelength of the laser might be within the range of 800 to 900 nm.

In one form, an optical filter is used to filter laser radiation which has passed through the terahertz generating crystal thereby reducing its effect of causing generation of further terahertz radiation if reflected back into the terahertz generating crystal. Reducing the likelihood of spurious generation of terahertz radiation reduces the possible effects of terahertz radiation that has not been reflected from a test sample, and minimises any adverse affect that the laser might have on a target such as a biological sample.

In another form, a protective window transparent to terahertz is provided to protect the terahertz generating crystals. This protective window may be glass although other materials may be used as desired and appropriate.

Ultrafast fibre lasers are now an alternative to the larger and more expensive Ti:sapphire mode locked lasers. A fibre pump laser would enable full fibre coupling useful for endoscopic implementation. Thus the enclosure may be shaped so that it fits into the gut lumen of an animal or human, and the reflection receiving window is positioned to contact or be adjacent to the gut wall, or alternatively it might be shaped for other endoscopic applications.

Another embodiment of the invention requiring a delay stage might be replace where a spatial transform method is used to detect the terahertz pulse. One technique is to measure the terahertz spectrum with a chirped optical pulse and a grating (Jiang and Zhang (1996) Applied Physics Letters 68(21) 2924–2926).

Another variation might be to observe the terahertz time domain pulse shape by directing the reflected terahertz pulse and laser probe pulse into the detector crystal at an angle and detecting the intensity with a linear diode array (Weling et al (1999) "Simultaneous recording of THz waveforms by multichannel electro-optic detection" in Ultrafast Electronics and Optoelectronics vol28 of OSA TOPS 95–97, OSA (Snowmass, Colo., USA), Shan et al (2000) Optics Letters 25(6), 426–428).

It will be understood that lenses may be required to achieve appropriate imaging or focussing in particular the terahertz radiation. Such lenses may take the form of transmission lenses or reflecting lenses.

It will also be understood that the apparatus may be coupled with a computer means that can analyse the data collected by the photodetector of CCD to provide for processing such as might be useful to diagnostic imaging or comparisons.

Turning now to the drawings.

A diagnostic apparatus is illustrated in schematic form in FIG. 1. It has a stainless steel enclosure (1) containing generator means for generating terahertz radiation. The generator means comprises a femtosecond laser (2) producing laser radiation (3) within the range of 800 to 900 nm and in pulse widths of less than 100 fs, and a zinc telluride terahertz generating crystal (4) which under the influence of the laser radiation produces terahertz radiation (5). The laser is outside the enclosure and its radiation is directed through a laser window (6).

The zinc telluride crystal also acts as a wall portion transparent to terahertz radiation through which generated terahertz radiation is directed out of the enclosure. There is a protective glass window (7) within a wall of the enclosure which allows for transmission of terahertz radiation. Between the protective window and terahertz generating crystal (4) is an optical filter (8) being an RG1000 filter, that absorbs laser radiation passing through crystal (4). In this way laser radiation reflected back from a sample or the protective window causing generation of spurious terahertz radiation is avoided or minimised, and additionally it protects the sample from any adverse affects that the laser may have.

A 95:5% beam splitter (9) is used to reflect a probe portion of the laser radiation to a delay stage (10) as part of a coherent detection scheme. The delay stage includes a mirror mounted to a mechanical stage which allows for adjustment of the path length. The delay stage allows for adjustment of up to 1 cm but is sufficiently fine for adjustment difference of terahertz or subterahertz wavelengths. The majority of the laser radiation passes through the beam splitter and to crystal (4). The beam splitter also passes laser radiation reflected from the delay stage, after passing through a polarisation rotator (11), and also reflects terahertz radiation.

The generated terahertz radiation passes through the optical filter and protective window. It may then radiate a target (12) which may be placed abutting the protective window (illustrated a short distance away from the window for explanative purposes only) and so the path distance is readily maintained by the simple act of placing the sample against the protective window however mounting a sample to a stage may be desired where a discrete sample is to be tested. Terahertz radiation reflected by the sample, including, to the limitation of penetration by terahertz, to its internal structures and constituents pass back through the protective window, optical filter and terahertz generating crystal (4) to be reflected by the beam splitter to fall upon a zinc telluride detector crystal (13).

The detector crystal (13) acts as a detector for terahertz radiation. The optical polarisation characteristics of the detector to the laser radiation are affected by the terahertz radiation so that the higher the amplitude of the terahertz radiation the greater the rotation of the laser pulse. A polarity filter (20) is positioned adjacent the detector crystal and arranged such that no laser light passes therethrough unless there is rotation of the laser probe within the detector crystal under the influence of the terahertz radiation. The larger the amplitude of the terahertz the more intense the pulse of laser passing through the polarity filter.

The delay stage (10) is adjusted so that the laser probe is varied in phase alignment for different terahertz pulses with respect of the same target such that a map of the terahertz pulse can be built up, if desired for comparison with known waveform alterations indicative of the presence of specific compounds. Alternatively the arrangement might be used to simply build up an image whereby a set delay is selected with a number of points of a sample measured to build up an image from the selected delay, the different point may be measured at the same time, or temporally spaced apart by moving the sample relative to the apparatus. This image may be recorded by its observation through a further protective glass window (14) with a CCD camera (15). Suitable lens arrangements might be positioned within the apparatus in order to focus or image the terahertz pulses as appropriate.

The enclosure is evacuated to substantially remove the presence of polarised molecules such as water. Accordingly, within the enclosure the environment favours transmission of terahertz radiation. Alternatively the enclosure may contain a terahertz transmissive atmosphere such as nitrogen.

Figure 2:
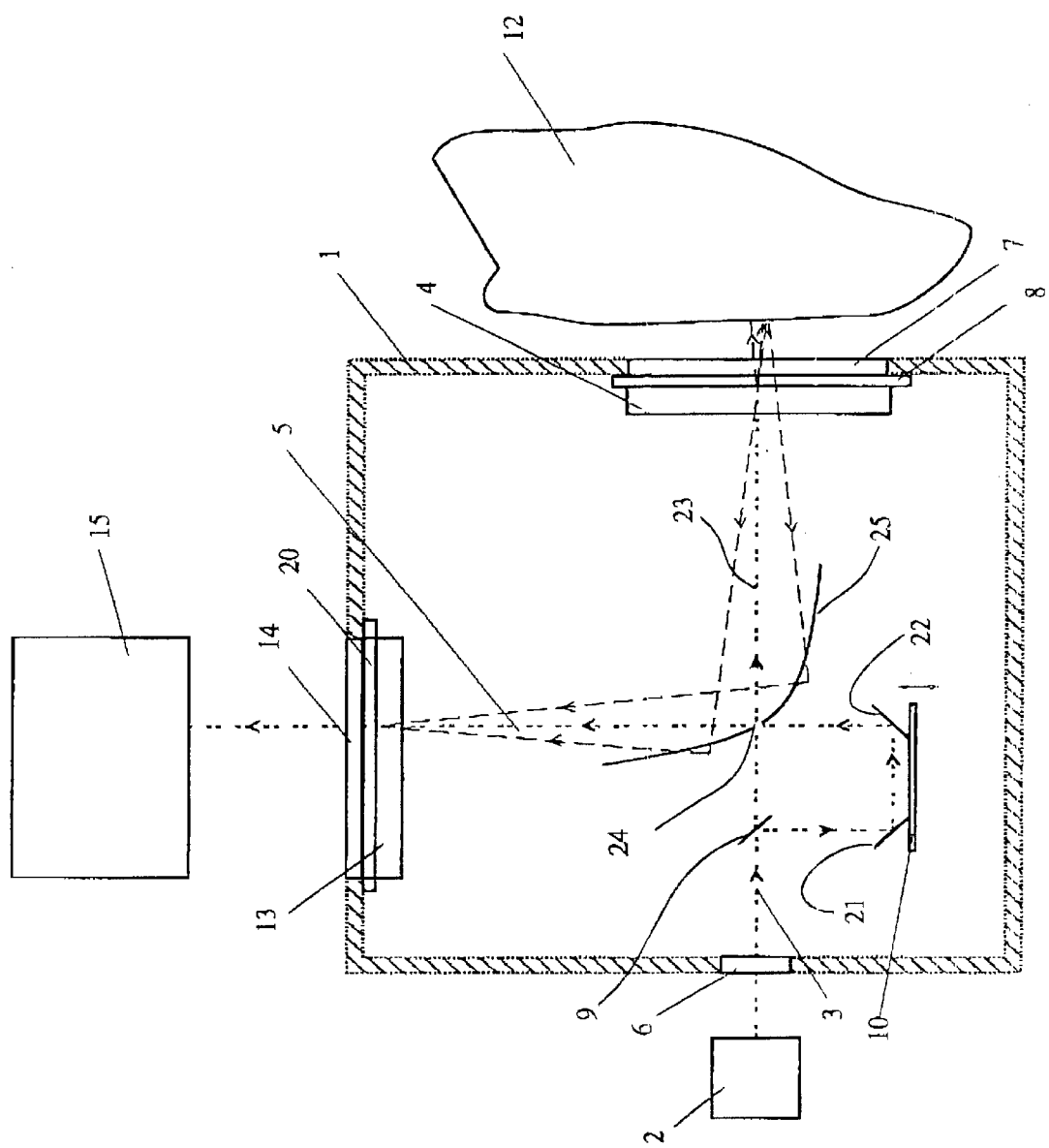
FIG. 2 is a schematically sketched cross sectional view of a second embodiment of diagnostic apparatus according to this invention.

FIG. 2 shows a similar arrangement as that in FIG. 1. This embodiment does not have a polarisation rotator because the polarised laser beam is suitable aligned to the polarity filter (20) so as to require rotation within the zinc tellurite crystal before it can pass therethrough. The geometry of the probe laser pathway is such that the polarisation rotator is not required. The beam splitter (9) is positioned further upstream than in FIG. 1 and made much smaller because it is not required to collect the reflected terahertz radiation. The delay stage is adjustable as with the first embodiment, the difference being however that it has two mirrors (21, 22) located thereon. The actuation laser pulses (23) pass through a mirror aperture (24) and strike the terahertz generating zinc tellurite crystal as in the first embodiment. Similarly the probe laser pulse also passes through the same aperture but orthogonally thereto. The terahertz mirror (25) takes on a hyperbolic shape to focus the reflected terahertz pulses onto the second tellurite crystal. It can be seen that the probe laser pulses and the focussed reflected terahertz pulses are co incident with respect to the second zinc tellurite crystal (13). This illustrates one means of focussing the reflected terahertz beam.

FIG. 3 illustrated a further geometry of a similar arrangement. In this third embodiment the beam splitter is located similar to that in FIG. 2 including a similarly arranged delay stage (10) except that the probe laser pulses are directed from the delay stage to a further mirror (30) which then reflects the laser probe pulse in a direction orthogonal to that of the reflected terahertz pulses. The reflected terahertz mirror (25) is planar in shape instead of the parabolic shape shown in the second embodiment. A transmission lens (31) focuses the terahertz radiation on an internally supported second zinc tellurite crystal (13). A photodetector (32) is positioned to receive laser probe pulses that are allowed through the polarity filter (20).

The detection scheme is a pump-probe scheme with the probe path length being approximately that of the terahertz radiation path excepting that it is variable in length over a wavelength of the laser radiation. Such a scheme is known to the art and does not in itself form a defining part of the invention disclosed herein. The detection scheme may be chopped to improve signal to noise.

In use a mirror is placed against the protective window in place of a sample. The system characteristics are then determined for later cancellation from sample measurements. The mirror is replaced by a sample which reflects terahertz radiation. This is detected and the system characteristics are cancelled out to leave the effects of the sample.

It will be appreciated that other detection schemes may be used as desired including photoconductive dipole antenna arrays. Likewise whilst a femtosecond laser is used in conjunction with optical rectification within the crystals for the generation and detection of the terahertz radiation other sources and schemes may be used including electronic sources.

The data collected by the CCD camera, photodetector or PDA array may be further processed to provided further information. Such processing will depend upon the particular application and so the form of detection scheme used and also the form of processing conducted.

One advantage of a reflection geometry is the potential for tomographic imaging where the depth profile of the sample is built up by analysing return pulses from internal structures in the sample (Mittleman et al (1997) Optics letters 22(12) 904–906). As is known tomographic systems utilise the magnitude and phase information of the reflected radiation to provide the information but this generally requires computationally intensive processing.

The detected data can be processed in a variety of ways, and thus a time component may be taken into account in order that a tomographic image can be built up. A method of such processing is set out in U.S. Pat. No. 6,078,047 to Mittleman et al., which is incorporated herein by reference.

An alternative method of analysing waveforms returned from sample materials is set out in U.S. Pat. No. 5,939,721 to Jacobsen et al. which is incorporated herein by reference.

Other means of analysing and utilising terahertz radiation are disclosed in U.S. Pat. No. 5,623,145 to Nuss, which is also incorporated herein by reference.

Additionally it might be desired to provide for near field imaging. Thus instead of the target being position a distance away from the first crystal it might be position a subwavelength distance from the first crystal and thereby enhance the resolution of any image built up. Methods of a near field terahertz imaging system is set out in U.S. Pat. No. 5,894,125 to Brenner et al., which is incorporated herein by reference.

Throughout this specification the term beam has been used and it is to be understood that the term includes pulsed electromagnetic radiation as well as a continuous wave of radiation.

What is claimed is:

1. A diagnostic apparatus including a terahertz generator for generating terahertz radiation, and an enclosure including a reflection receiving window and a terahertz detector for detecting terahertz radiation, the terahertz generator directing terahertz radiation onto a target, reflected terahertz radiation being reflected through the reflection receiving window into the enclosure and to the detector, a modified atmosphere being provided within the enclosure to permit ready transmission of terahertz radiation.

2. A diagnostic apparatus as in claim 1 wherein the terahertz radiation is generated inside or on a surface of the enclosure, and is directed out from the reflection receiving window.

3. A diagnostic apparatus as in claim 1 wherein the terahertz generator is radiated by terahertz inducing laser radiation directed thereonto by a laser, the terahertz generator being either a terahertz generating electro-optic crystal or a terahertz generating photoconductive dipole antenna.

4. A diagnostic apparatus as in claim 3 wherein the terahertz generator is a terahertz generating electro-optic crystal, said terahertz generating crystal forming at least part of the reflection receiving window.

5. A diagnostic apparatus as in claim 3 having a beam splitter positioned between the laser and the terahertz generator to split off a probe laser beam from the terahertz inducing laser radiation, said probe laser beam travels through a probe laser path to the detector means, the detector providing a quantitative output, the output being determined by the amplitude of that part of the reflected teraherz radiation wave coaligned with the probe laser at the detector.

6. A diagnostic apparatus as in claim 5 having a delay positioned in the probe laser path said delay altering a length of the probe laser path over terahertz subwavelength distances to thereby vary the co-alignment of the probe beam and the reflected terahertz radiation wave.

7. A diagnostic apparatus as in claim 6 wherein the detector includes a detector electro-optic crystal which in response to terahertz radiation alters its optical characteristics such that laser radiation directed upon the detector crystal reveals the terahertz radiation.

8. A diagnostic apparatus as in claim 7 wherein a polarity filter is positioned between the detector electro-optic crystal and a photodetector such that the probe laser beam does not pass through the polarity filter unless the detector electro-optic crystal causes the probe laser beam to rotate, the terahertz radiation causing polarisation of the probe laser beam to rotate and the degree of rotation is proportion to the amplitude of the reflected terahertz radiation.

9. A diagnostic apparatus as in claim 6 wherein the detector includes a detector PDA whereby reflected terahertz radiation together with the probe laser when co-aligned can provide for an electric pulse.

10. A diagnostic apparatus as in claim 9 wherein the detector is provided as an array of PDAs.

11. A diagnostic apparatus as in claim 3 wherein the laser is positioned outside the enclosure and the laser radiation transmitted through a laser transmissive window into the enclosure.

12. A diagnostic apparatus as in claim 5 wherein the reflected terahertz radiation and the probe laser beam are co-incident at the detector.

13. A diagnostic apparatus as in claim 5 wherein the probe laser beam is incident transverse of the incidence of the reflected terahertz radiation at the detector.

14. A diagnostic apparatus as in claim 6 wherein the beam splitter directs the probe laser beam onto a mirror positioned to direct the probe laser radiation onto the terahertz detector.

15. A diagnostic apparatus as in claim 14 wherein the probe laser mirror reflects the laser radiation through the beam splitter means onto the terahertz generator, and the reflected terahertz radiation is directed by the beam splitter means to the detector and thereby is co-aligned with the laser radiation.

16. A diagnostic apparatus as in claim 1 wherein the probe laser mirror is supported on a delay stage together forming the delay means for varying the length of the probe laser path.

17. A diagnostic apparatus as in claim 1 wherein the atmosphere within the enclosure is evacuated.

18. A diagnostic apparatus as in claim 1 wherein the atmosphere within the enclosure consists primarily of a non-polar gas.

19. A diagnostic apparatus as in claim 3 wherein the laser produces laser radiation pulses of pulse width less than 100 fs.

20. A diagnostic apparatus as in claim 3 wherein the laser produces laser radiation pulses of pulse width less than 20 fs.

21. A diagnostic apparatus as in claim 3 wherein the wavelength of the laser is within the range of 800 to 900 nm.

22. A diagnostic apparatus as in claim 1 wherein the terahertz radiation has a bandwidth spanning the range of 0.1 to 10 THz.

23. A diagnostic apparatus as in claim 4 wherein an optical filter is used to filter laser radiation which has passed through the terahertz generating crystal thereby reducing its effect of causing generation of further terahertz radiation if reflected back into the terahertz generating crystal.

24. A diagnostic apparatus as in claim 4 wherein a protective window transparent to terahertz is provided to protect the terahertz generating optoelectric crystal.

* * * * *